United States Patent [19]
Experton

[11] Patent Number: 5,995,965
[45] Date of Patent: *Nov. 30, 1999

[54] SYSTEM AND METHOD FOR REMOTELY ACCESSING USER DATA RECORDS

[75] Inventor: Bettina Experton, Del Mar, Calif.

[73] Assignee: Humetrix, Inc., San Diego, Calif.

[ * ] Notice: This patent issued on a continued prosecution application filed under 37 CFR 1.53(d), and is subject to the twenty year patent term provisions of 35 U.S.C. 154(a)(2).

[21] Appl. No.: 08/751,339

[22] Filed: Nov. 18, 1996

[51] Int. Cl.$^6$ ..................................................... G06F 17/30
[52] U.S. Cl. ............................................ 707/10; 709/227
[58] Field of Search .............................. 707/1, 2, 9, 104, 707/10; 395/200.57; 709/227

[56] References Cited

U.S. PATENT DOCUMENTS

| | | | |
|---|---|---|---|
| 5,465,082 | 11/1995 | Chaco | 340/825.54 |
| 5,588,146 | 12/1996 | Leroux | 707/1 |
| 5,602,918 | 2/1997 | Chen et al. | 380/21 |
| 5,659,741 | 8/1997 | Eberhardt | 707/104 |
| 5,682,549 | 10/1997 | Tanaka et al. | 710/8 |
| 5,710,884 | 1/1998 | Dedrick | 395/200.47 |
| 5,813,009 | 9/1998 | Johnson et al. | 707/100 |
| 5,832,488 | 11/1998 | Eberhardt | 707/10 |
| 5,899,998 | 5/1999 | McGauley et al. | 707/104 |

*Primary Examiner*—Jack M. Choules
*Attorney, Agent, or Firm*—Jeffrey Slusher

[57] ABSTRACT

User data records, such as health or financial data, are stored in a data base at one or more remote facilities, for example, at one or more hospitals or one or more central processing facilities. For each of a card-holding group of users a card is provided. The card is preferably a "smart card," which has a memory and, preferably, an onboard processor. The card is encoded with the respective user's identifying information, as well as with information that identifies at least one remote network address of at least one remote facility where the user's records are stored. The user uses the card to activate a local processor, which then automatically accesses a network, generates and applies to the network a remote record request corresponding to the activating user's identification code, along with the appropriate remote network address(es). The remote processor, which is also connected to the network, verifies the record request and downloads all or a requested or predetermined part of the corresponding user data records to the local processor. This data may then also be downloaded at least in part to the memory of the user's card. Updates to the user's data records may also be uploaded from the local processor to the remote processing facility, or downloaded to the card, or both. The network is preferably a publicly accessible network such as the Internet, whereby the remote network address can be an Internet address in any conventional format.

11 Claims, 1 Drawing Sheet

SYSTEM AND METHOD FOR REMOTELY ACCESSING USER DATA RECORDS

BACKGROUND OF THE INVENTION

1. Field of the Invention

This invention relates to a system and a method for automatically accessing user data records, in particular, via a network.

2. Description of the Related Art

Imagine any of the following situations: A worker collapses on the job with labored breathing. An elderly colleague begins to speak incoherently, becomes disoriented, and turns very pale. A hiker is found unconscious, with a compound fracture and arterial bleeding. An expectant mother staggers into an emergency room with an alarmingly high fever and clear signs of a severe systemic infection.

In all of these situations, emergency medical personnel—those on the scene, in the ambulance, and in the hospital—need fast, accurate information about the medical history of the patient. Only in exceptionally lucky cases, however, will an up-to-date history be available—usually, only when the patient has been to the receiving health-care facility before, was given a thorough medical evaluation and has not been treated elsewhere since. Because of this lack of up-to-date information, proper diagnosis and treatment may be problematic; for example, giving the patient a certain drug might cause severe side effects. For example, emergency personnel may not know that an unconscious patient has been using some dangerously interacting medication, which was prescribed by a physician who is not affiliated with the hospital where the patient has just been admitted. As yet another example, the emergency medical team may have no way to know that the expectant mother is severely allergic to the antibiotic they intend to administer to her.

Unless the patient is wearing a warning bracelet, or is carrying some information identifying her regular physician or clinic, then there is no way at present for the emergency medical personnel to get at the needed, possibly vital, information. The primary care physician may not be available; the far-away clinic may not have the patient's file readily available, and there may not be time to excavate it from the cavernous file room found in many large, modern hospitals.

It is not just in emergencies, moreover, that rapid access to up-to-date health-care information is desirable. Such information is also useful, for example, during normal visits to a patient's ordinary health-care provider, or to a specialist to whom the patient has been referred. At such times it can both save much time and maybe even improve a diagnosis or treatment if the providers, for example, different physicians in a health-care network, can readily access the health and insurance information of patients.

One solution to this problem that has been proposed is for patients—past, present, and potential—to be issued a card that incorporates some form of memory device on which essential health care information is stored. The memory devices in these cards may be magnetically or optically encoded strips that can be read by appropriate conventional readers. Such passive memory devices, however, typically carry only a small amount of data, cannot readily be updated, or require expensive, specialized equipment to change their memory contents. Because of their limited memory capacity and non-updatable nature, the cards serve only to identify the patient, his primary health care provider, and his insurance information. Moreover, smart cards can easily be updated and their storage capacity is greater than that of, for example, magnetic-strip cards, but even their memory capacity is limited and restricts their use to the storage of only a summary medical history.

Yet another problem of existing health care data cards is that, to the extent that they can access remote information at all, doing so requires a dedicated line to some central data base. This line may not be available when needed in an emergency; it may be linked only to one or a few facilities or sites (for example, different sites within a large facility); and other facilities or sites may be linked only by installation of expensive, dedicated hardware.

Still another shortcoming of existing devices for accessing medical records is that their memory contents cannot be updated or otherwise changed except by expensive, specialized equipment, which usually only the card provider has at some remote location. These cards will thus carry outdated or incomplete information for some time after every use.

Some or all of these problems are also encountered in other contexts where complete and accurate information needs to be retrieved from a remote site. For example, the process for getting approval for a loan or mortgage is often delayed by the need to gather the potential borrower's credit records.

What is needed is a system and a method that allow emergency medical personnel to quickly access a potentially large amount of medical data concerning a patient using a readily and widely available communications link. The system should be easy to activate using a device that the patient can carry conveniently. It should preferably also be possible to expand the system. Furthermore, the system should ideally also be flexible enough that it can be applied for quick and secure access to other kinds of user data records.

SUMMARY OF THE INVENTION

According to the invention, user data, such as health or financial data for any number of patients or members, is stored in a data base at one or more remote facilities, for example, at one or more hospitals or one or more central processing facilities. Each patient/member is provided with a card, preferably a "smart card," which has a memory and, preferably, an onboard processor. The card is encoded with the respective patient's identifying information, and preferably includes other data such as card access authorization codes, information that identifies at least one remote network address of at least one remote facility where data records are stored, and specific patient file locations (data sub-addresses) at each network address.

The user (who may be, for example, the health care provider where the patient is being treated, or the patient himself), uses the card to activate a local processor, which then automatically accesses a network, generates and applies to the network a remote record request corresponding to the activating member's identification code, along with the appropriate remote network address(es). The remote processor, which is also connected to the network, verifies the record request and downloads all or a requested or predetermined part of the corresponding user data records to the local processor. This data may then also be downloaded at least in part to the memory of the patient's portable card, after updating (as required) by the user of the patient's electronic record.

The network is preferably a publicly accessible network such as the Internet, whereby the remote network address can be an Internet address in any conventional format. This allows additional remote, data storage and processing facilities and their patients/members to join the system. Each facility may then store the records of its members, or the facilities may maintain a common, central data base accessible through the network at the network address.

DETAILED DESCRIPTION

Figure 1:
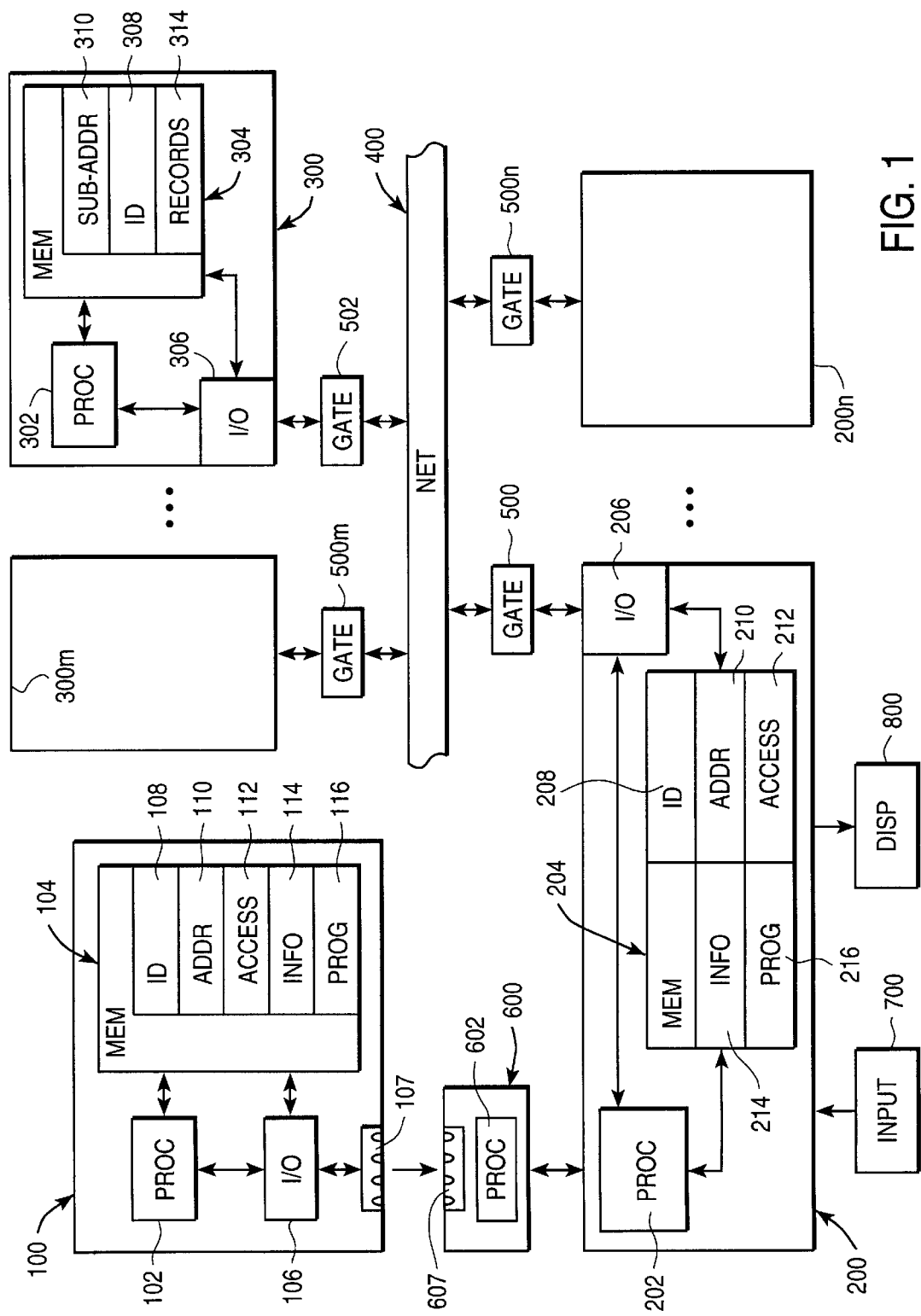
FIG. 1 is a block diagram that shows the components of the system according to the invention that are used when a user initiates a request for user data records.

The invention is described below primarily in the context of rapid and secure retrieval and updating of health-care data records for one or more users or members of a health-care data system. Typically, health-care data includes (but is not limited to): demographic data, such as the name, address, date of birth, name of next of kin, and other "administrative" information for the patient; clinical data, such as results of examinations or laboratory tests; insurance and provider data, such as the name of the insurance provider and name of a primary care physician; and "encounter, financial" data, which includes a health service utilization history (for example, in the form of dates and service codes) of which services the patient has used in the past. This is the preferred application of the invention, since it meets the most critical need, but this field of application is but one of many examples of applications in which the invention is useful and advantageous.

The invention is, for example, well-suited to handle rapid and secure access to financial data, as mentioned above, or in any other area where data records are to be downloaded remotely. The financial data may likewise be segmented or "compartmentalized" to include, as separate files, data about a customer's (who is a member of the system) assets, for example, bank account balances, credit and payment history, available credit, "administrative" data such as mailing address, and even security data such as the personal information (for example, mother's maiden name) that a customer often is asked to give when opening an account in order to verify his identity later. In the context of security, note that security data could include data files in any conventional format that show the image of the customer's signature or, indeed of the customer herself.

Still another example of the usefulness of the invention would be in the area of personalized financial transactions such as the trading of stocks or other securities. Using the invention, a trader could quickly, securely and automatically access her own remotely stored portfolio status and history, as well as other predetermined data records, for example, those in which the current trading values of a selected group of securities are recorded and continuously updated.

As yet another example, firemen on the scene could use the invention to quickly and securely download data records concerning the floor plan and contents of a building, along with information about the building's owner, the number of employees, and so on. The manner in which the invention described below is be adapted to such non-medical applications of the invention will be apparent to those skilled in the art.

In this invention, the "user" of a portable access device is anyone who handles the portable access device in order to initiate a data transfer or cause a data change. The user may thus be either the person to whom it is issued (for example, the card-holder of a smart card), or the service provider, who takes the card from the card-holder and activates a local processor with it, or both. Note that the invention envisages that both the card-holder and the service provider may need or wish to access different data records whenever a cardholder needs to initiate a data transaction. For example, a physician may need to access not only a patient's clinical data records, but may also need to download the patient's insurance records and upload to the central data base his own updates to a billing data base for the patient.

In FIG. 1, a portable access device is indicated generally by reference number 100. For the sake of simplicity, only one such device is shown, but in most cases, the organization, such as a hospital, insurance company, or hospital or financial group, that uses the system according to the invention will issue at least one portable access device to each member or patient in its medical record system. In the preferred embodiment of the invention, this device is a smart card, which includes a processor 102, a memory 104 and an input/output unit 106, which are both connected to the processor. The processor 102 is typically a programmable microprocessor chip that is embedded or otherwise mounted in the card, the body of which is normally plastic. Depending on the implementation of the processor, the input/output unit may be incorporated into the processor 102. The card 100 also includes electrical or optical contacts 107, via which data between the processor 102 and external units (described below) is transferred.

In the preferred embodiment, the portable access device is a smart card, so this implementation is assumed in the discussion below. The general structure and operation of a smart card are known and are therefore not described in further detail. See, for example, the article "Smart Cards", *Scientific American,* August 1996, pages 40–45. Changes in the system that would be required to implement other types of portable access devices, such as magnetically or optically encoded data cards are either mentioned where appropriate or will be obvious to those skilled in the art of peripheral access devices for processors.

The memory 104 is also mounted in the card 100 and contains the operating instructions for the processor, as well access data and possibly also downloaded data, which are described below. The memory 104 preferably comprises separate portions. In the preferred embodiment of the invention, these portions include memory segments that hold the card-holder's identification data 108, remote network address data 110, access data 112, for example, encryption and/or decryption keys, an information storage portion 114, which stores, for example, a predetermined portion of the patient's health-care data, and a program memory portion 116 that contains the operating instructions for the processor 102.

The program memory portion 116 of the memory 104 is preferably implemented using a non-volatile and preferably reprogrammable technology such as EPROM or EEPROM, as long as the packaging of the device includes standard shielding as required to protect such memory devices from, for example, electromagnetic or ultraviolet radiation that might accidentally alter the memory contents. Other memory portions are preferably implemented in a conventional readable and writable technology (such as RAM) to permit updating of the memory contents for this data. The ID portion 108, and other memory portions as needed in a given application, may, however, also be implemented in a non-volatile memory technology in order to increase both the physical robustness and also the security of the device. Of course, the information storage portion 114, which is to contain downloaded or changeable data, is preferably implemented using convention RAM technology.

A local processing unit is indicated in FIG. 1 as unit 200. Any number of local processing units, 200, ..., 200n may be implemented according to the invention, but only one is shown in detail in FIG. 1 since the others will have the same general structure. The local processing unit includes a local processor 202, a local memory 204, and a local input/output circuit 206.

The local processing unit 200 is preferably a conventional microprocessor-based fixed or portable computer of the type known as a "personal computer" or "PC," since such systems are widely in use, are affordable, and typically have all of the hardware necessary to access a network, upload data requests, and download data. Other conventional or specially designed computer systems may, however, be used to implement the invention.

Whereas the portable access device 100 will typically be carried or presented by the card-holder to a service provider, the local processing unit 200 will normally be located at the site of a local service provider, such as at a physician's office, a branch bank, etc. It is, however, also possible for the card-holder to have and control the local processing unit.

The input/output circuit 206 in the preferred embodiment of the invention is a conventional modem connected to a standard I/O port of the processor 202. A modem is preferred because, once again, such systems are widely available. In applications that use a modem, the processing unit 200 includes conventional modem control circuitry.

The memory 204 includes portions containing user identification data 208, network address data 210, network access protocols and data 212, an information storage portion 214 that stores, for example, a predetermined portion of the patient's health-care data, and a program memory portion 216 that contains the operating instructions for the processor 202. In the preferred embodiment of the invention, the local memory 204 is segmented roughly the same as the memory 104 of the portable access device 100. To the extent such memory portions would represent pure duplication, then the corresponding portions of the local memory 204 can be omitted.

On the other hand, including similar—but not identical—data storage in both the portable access device 100 and the local processing unit 200 provides greater flexibility. For example, the provider (for example, physician) who controls the local processing device may herself desire to automatically download and upload certain data records. These physician-only data records may include, for example, the physician's own identification and authorization codes and health-care data records containing information unsuitable for presentation to the layman patient, whenever any user data request is generated.

A remote processing unit or facility is indicated in FIG. 1 as unit 300. Any number of local processing units, 300, ..., 300m may be implemented according to the invention, but only one is shown in detail in FIG. 1 since the others will have the same general structure. The local processing unit includes a processor 302, a memory 304, and an input/output circuit 306.

Depending on the number of data records to be stored remotely, the processing unit 300 may be a conventional microprocessor-based fixed or portable computer of the type known as a "personal computer" or "PC," or a mini- or mainframe computer, with associated conventional supporting circuitry. In order to improve the speed, integrity and robustness of the system, the processing unit 300 is preferably at least powerful enough to be or include a server that can support a unique network address, and directly receive data requests over a network 400 (see below) such as the Internet.

If more than one remote processing facility 300 is included in any given implementation of the invention, then they may be connected for communication in any conventional manner (including via the network) in order to eliminate the risk of mutually contradictory stored data. This might be the preferred case, for example, where the facilities are cooperating groups of hospitals or banks, where each maintains its own data base and network server and has its own unique network address or group of addresses. The servers at the various facilities can then contact each other periodically in order to update data that is held in common. For example, a central list of user information sites can be maintained at one of the facilities or at some other agreed-upon site, along with a date and time stamp of the most recent access of any given set of records. Whenever the records are accessed or changed, the processing unit at the facility that holds the records can contact the central list and update the date and time stamp for those records, as well as making any other relevant notation, for example, of a failure of a particular customer to make a timely payment.

The input/output circuit 306 in the preferred embodiment of the invention may be a conventional modem connected to a standard I/O port of the processor 302, but is preferably a conventional multi-channel input and switching device able to establish communication with and sequence requests from more than one remote processing unit 200 at a time. This capability will be found in most known processors that are configured as network and data base servers.

The memory 304 preferably also comprises separate portions. In the preferred embodiment of the invention, these portions include memory segments that hold user identification data 308, file or sub-address data 310, and the data records 314 that various users might wish to access. Other memory portions, for example, portions that contain the various programming and operating instructions for the processor 302 and I/O unit 306 are also included as needed, but are not illustrated since they will be similar in principle to those of the local processing unit 200—the basic operational programming of a processor is well known.

Each record to be accessed may be a single file, a series of files, a linked series of data fields, or any other conventional data structure, which is preferably associated with an identifying record sub-address. Presentation of a particular sub-address thus signals to the processor 302 that the associated record is to be retrieved. A single user transaction may consist of a request for several separate records from the record memory 314. Furthermore, a transaction may include requests for records based on sub-addresses stored in the portable access device and also requests by the provider for other records as generated from the address memory 210 of the local processing unit 200.

Each remote processing unit or facility 300 and each local processing unit or facility 200 is connected to a network 400, which may be a publicly accessible network such as the Internet, or a dedicated network that is proprietary for the administrators of the system. A public network is preferred since it will then have the widest availability—in the case of the Internet, this availability would even be international via normal telephone lines. Connection to the network 400 is preferably via conventional gate circuits 500, ..., 500n, 502, ..., 500m. Connection between the gate circuits and the network is preferably arranged via known devices such as existing telephone switches and lines, although dedicated connections, such as wires, optical fibers, or wireless links may also be used if the extra speed is needed, the cost is not prohibitive, and these alternative connections can be expanded to other remote and local processing units as needed.

Where the portable access device 100 is a smart card or some other specialized device, the system according to the invention includes a card reader 600, which may be a unit that is incorporated into a respective one of the remote processing units 200, or is attached as a peripheral unit via any conventional processor port. Examples of suitable card readers (in the case that the portable access device is a smart card) include: the SCR 60 Terminal (for use with PCs) manufactured by the company Schlumberger; the Philips PE112 or PE122 smart card reader/encoders for connection to work stations or PC's; the Philips PE112–302 (which can be mounted in the floppy drive slot of a PC); or known PCMCIA card readers that are inserted in the PCMCIA slot of desk- or laptop computers.

If the portable access device is other than a smart card (which has its own onboard processor 102), then the appropriate reader (such as for magnetic strips or optically readable and writable surfaces) will be connected to the processing unit 200. Note that it is not necessary according to the invention for all users to use the same type of portable access device. Note also that the reader 600 may also be connected to the processing unit 200 in a wireless manner, for example using known infrared, visible light, or radio-frequency links, in which case conventional interface circuitry will be included.

Especially in the context of accessing patient health care records on an emergency basis, the reader 600 is preferably connected to the highest-priority interrupt hardware port of the processor 202; alternatively, whichever port the reader is connected to is assigned the highest interrupt priority by the operating system of the processor.

The reader 600 may include its own processing and drive circuitry 602, and will include contacts 607 that match the contacts 107 of the portable access device 100 for transfer of data (serial or parallel, depending on the device) and power (as needed).

Note that data transfer between the portable access device 100 and the reader 600 may also be arranged using an optical (for example, optical fiber) or other wireless (for example, infrared or RF) connection between the two devices. In these cases, the contacts 107, 607 will instead be the respective transmitting/receiving ports or sensors of the chosen transmission devices.

Moreover, if the portable access device 100 is not a smart card, with contacts (or contact-less transmitting/receiving ports) 107, but is rather a device with magnetically or optically readable surfaces, the reader will include as element 107 the corresponding conventional pick-up, sensing and/or writing head or sensor.

As is explained further below, one advantage of the invention is that it allows for automatic access of data records (such as health care records) without the need for complicated data entry—the user simply inserts the portable access device 100 into (or, in the wireless case, brings near) the appropriate reader 600 and the processing unit preferably handles the rest of the data transaction. If needed, for example, for post-transaction record-keeping, a standard input unit 700, such as a keyboard, may also be connected to the processing unit 200; indeed, a keyboard is almost certain to be connected to the processing unit anyway, since the processing unit will seldom be provided solely to use the invention. The keyboard will also typically be used for data updating, where data is downloaded into the memory of the local processing unit 200 and that of the portable access device 100, or is uploaded into the memory of one or more remote processing facilities, or both.

Other input devices besides a keyboard may also be used. For example, the input device 700 may be some other data processing device such as a tabletop or laptop computer, hand-held computer, or other data-recording, in which the service provider may enter his comments, notes, and data updates during or after treatment. These input devices may be connected to the local processing unit in any known manner such as by electrical cable, optically, or wirelessly.

In order to view the retrieved user data records, a display and/or printing unit 800 is connected to the remote processing unit 200. These may be conventional devices such as CRT or LCD monitors, and/or standard printers.

The method according to the invention is best described by an example. The example of accessing emergency health data records is most illustrative. Assume that one—for example, a paramedic or emergency room physician—needs to access data records for a patient. (As another example, the user may be the one whose records are to be accessed, for example the applicant for a loan who is sitting in the bank, which has a local processing unit 200.)

The user first takes the portable access device 100 of the patient (loan applicant, building, etc.) and couples it with the reader 600 as appropriate, for example, by inserting it into a slot so that the contacts 107, 607 are electrically connected. The reader then generates a signal to the processor 202 that a portable access device has been activated. The processor then executes an appropriate, conventional interrupt routine to read the inserted device, which, for the sake of this example, is assumed to be a smart card. The smart card then inputs activating data to the processor 202. Unless the processor is already completely dedicated to the smart card of a single user, this activating data will include user identification data, which the processing unit verifies, for example, using a standard decryption routine.

Activating data will also include remote network address data which identifies the network addressees) of each remote processing facility 300, . . . , 300m where the activating user's records and provider-requested records are stored. The network address data for user-requested records is preferably stored in the memory 104 of the smart card, so that it will be available to any processing units that the card is used to activate. The network address data will include the address to the remote processing unit where each record is stored, as well as the sub-addresses for the various requested records within the respective remote processing unit. If the portable access device is always to be used with a single local processing unit, with a known, dedicated group of them, then the network address data may instead (or in addition) be stored in the address memory portion 210 of the processing unit 200.

As is mentioned above, the provider, who will normally (but not necessarily) controls the local processing unit 200, may also want to request remotely stored records whenever a user (card-holder or provider) activates the system. The network address(es) of the each remote processing unit 300 where the corresponding records are stored are in such case preferably also stored in and retrieved from the address memory 210. As before, the address data may contain sub-addresses identifying the various records that the provider wants to access. Note that addressing a remote data record need not be solely for the purpose of reading, that is, downloading, it from the remote processing unit(s) to the local processing unit. Rather, remotely stored records may be addressed and accessed in order to upload changes to them. For example, if one record stores the list of all physicians who have requested records for a patient, along with the date and time of the request and the procedures performed or medications prescribed, then the identification of the physician/provider will be uploaded as an addition to this record from the ID memory 208. The physician could, for example, upload the procedure code and the newly prescribed medication information by entering this information via the input unit 700.

The access memory portion 212 of the processing unit 200 includes conventional software for modem or other I/O initialization, I/O dialing instructions, network access protocols, and data retrieval commands for automatically accessing the network and addressing each identified remote processing facility via the network. The required steps include those that a user would normally have to enter via a keyboard or mouse/display combination in order to log onto a network with the user's ID, enter the remote network address of the needed remote processing facility, and corresponding commands for communicating to the remote facility a request for downloading the corresponding data records. Rather than entering them by hand, however, all of these steps and commands are pre-stored in the access memory 212 of the processing unit 200; alteratively, all or some of them may be stored in the access memory 112 smart card 100 itself. The manner in which such network access and control "scripts" are written is known and is therefore not described in further detail here.

When the processing unit senses activation of a smart card, it thus interrupts all other applications, initializes the I/O device 206, accesses the network 400 with the address of the corresponding remote processing facility 300, senses when two-way communication is established, passes the command signals for a data record request along with the user ID and record sub-addresses (if implemented), and receives and displays and/or prints out the retrieved data records. The commands for all of these steps may be pre-programmed into the access memory 212, so that there is no need for any additional data entry by the user once the smart card has been activated (inserted into the reader).

As is mentioned above, different records may be requested for the card-holder and the provider, who typically (but not necessarily) will control the local processing unit 200. Furthermore, either the user or the provider may request records stored in different remote processing units 300, . . . , 300m. Different records in different remote processing units may also need to be updated by uploading from the local processing unit when a record transaction is requested or completed. This may also be carried out using normal programming techniques.

Assume, for example, that each remote processing facility 300 has a network address of the form remotei, where i is the number of the facility. Let the records for each user in the system be sorted (stored in the record memories 314) under an address userj, where j is a user identification number. Illustrative examples of various sub-addresses and corresponding files could then be:

userj/demog: user no. j demographic data
userj/clinical: user no. j clinical data
userj/finance: user no. j encounter financial data
userj/insur: user no. j insurance data
userj/access: date and time of most recent and previous requests for data or changes to the record userj
userj/keys: passwords and other keys used to identify a user and verify authorized access to files in userj, as well as, unless otherwise provided for, encryption and decryption keys Records may be stored and addressed for each provider, in which case they would be stored and addressed similarly.

Once two-way communication is established and sensed between the local processing unit 200 and the first of the remote processing units (for example, at remote1) where needed records are stored, the local processing unit 200 transfers via the network identification data (from the user ID memory 108 and the provider ID memory 208) and verification data (described below) as well as the addresses and sub-addresses of the records and files to be downloaded. The addresses may be transferred either sequentially, whereby the local processor waits for one downloaded data set before requesting the, or all at once, depending on how the transfer protocols are established in any given application. When all files are downloaded from one remote processing facility, the local processing unit 200 then proceeds to address and download data from (and upload data to) the next remote facility (at, say, remote2) as needed. The programming steps required to sequence and carry out such data transfers over a network are well known and are therefore not described further.

All activating data, as well as the data records themselves, may be encrypted using any conventional techniques. As but one example, the data may be encrypted using a public key routine. As is well known, in a public key system, two keys (equivalent to mathematical "passwords") are used, an encryption key and a decryption key. Knowledge of both—or at least the decryption key—is required to decrypt an encrypted message, but knowledge of the encryption key is sufficient to encrypt a message. Consequently, once a sender has applied the encryption key to a message to encrypt it, then the sender himself is unable to decrypt the message again. The encryption key may thus be made publicly available without loss of security.

To continue this example, one method for providing secure transfer of sensitive health or financial data is for each user and each remote processing facility 300 to have at least one unique set of keys. The user's keys may, for example, be stored in the ID memory 108 or the access memory 112 on the access device 100. Similarly, the provider may have at least one set of keys stored in the ID memory 208 or the access memory 212. When communication is established between the provider and a remote processing facility, one way to ensure security would be for the various systems to exchange public encryption keys (thus allowing them to be changed according to some predetermined scheme, even from one use to the next). All data transfers could then be encrypted, with only the receiving processor being able to decrypt the messages, since only it will have its decryption key. Alternatively, the encryption keys may be pre-stored in the appropriate memory segments—transmission of a properly encrypted message would then aid verification of the identity of a data requester. (Any known routine for "digital signatures" may also be used.)

The system may be set up so that only the provider is able to read certain requested data, for example, a loan applicant's full credit history. This can be done in several ways. First, the nature of the requester (user or provider) can easily be established either by examining the address of the data requester and comparing it with a list of authorized providers who can access the remote processing facilities. One way is to give the corresponding sub-addresses only to appropriate providers. For example, a pharmacist/provider may be allowed to have access only to the sub-addressed files containing medication history, whereas the primary care provider might have full access to the patient's records.

Another is simply to write the data transfer script in such a way that such data is never written to the portable access device 100, or to provide different scripts to different providers, so that, for example, the pharmacist's local processing unit would not be able to generate the sub-addresses for unauthorized files. Still another way is to associate different encryption keys with different files. Only those local processing units that have (or receive from a portable access device) the correct encryption keys, would be able to generate correctly encoded requests for those files.

Once the remote facility 300 senses that it has been addressed (using conventional server technology), it verifies that the requesting user ID corresponds to one stored in its user ID memory 308, possibly after verification using known encryption/decryption techniques. After verification, it senses which sub-record addresses are to be downloaded from the record memory 314, along with any updating information. The sub-addresses in the local processing unit that point to records to be changed are then updated according to data uploaded from the local processing unit.

Updated information may also be downloaded to the portable access device 100, to the local processing unit 200, or both. This data may include, for example, the date and time of the immediate data transfer, any administrative changes (for example, change of primary care physician or of financial status), clinical changes (for example, a new diagnosis code, an updated medication list, and so on), and any other data that has been changed or added since the most recent request for data records. To accomplish this, a date and time block stored in the memory 104 of the card or the memory 204 of the processing unit 200 may be updated with the most current values. Updates may also be processed by the local processor before passing them on to the smart card processor 102, which stores it in the appropriate positions in the memory 104.

Updates may also be generated by the service provider, who will typically enter the updates via the input unit 700. For example, after treatment, a physician will normally need to update a patient's data records to reflect such things as the diagnosis, any prescribed medications, any performed procedures, and so on. The physician may then enter these updates into the local processing unit 200 according to any conventional routine. For example, the physician could simply type the changes into appropriate conventional data fields of an update screen. Each data field could be associated with predetermined user records (either for the patient or the physician), each of which has its network or local address (in memory 204, in memory 104, or in both). The processing unit 200, following the access routine described above, would then address the network sequentially with the appropriate remote addresses, access the corresponding user records 314, and indicate in a known manner to the remote processing unit 300 that the corresponding memory contents are to be changed.

Data records at remote processing facilities may of course also be updated directly using known devices and procedures. For example, some data may come in to a remote processing facility in a conventional written form, such as from an organization not affiliated with system, or which does not have network access. Such updates could then be entered using any conventional data entry methods. Updates may also be "continuous" or "automatic," for example, where the invention is used for automatic access to a remote data base of quickly changing stock prices. In this case, the remote processor 302 may be in network communication with a provider of such stock price data and would continually update the corresponding record 314 with the price quotes and quotation times.

Updates may also be downloaded from any remote processing facility 300, . . . , 300m, to the portable access device 100, via the network 400 and the local processing unit 200 to which the device is in communication. In such case, the local processing unit 200 opens (if not already opened) data communication with the access device 100 via the reader and directs the processor 102, using conventional protocols, to receive the updated data and enter it into the corresponding positions in the memory 104. Of course, data updates entered directly into the local processing unit 200 via the input device 700 may also be downloaded in this manner onto the portable access device 100.

I claim:

1. A system for accessing user data records comprising:

remote processing and storage means that is connected to a network and has a remote network address,
for storing user-specific data records in a remote memory for each of a plurality of users;
for receiving and verifying remote user-specific record requests directed to the remote network address; and
for accessing and downloading user-specific data records for each verified remote record request;

for each of a predetermined group of users, a portable access device that includes an onboard processor;

at least one local processing means:
for sensing activation of the portable access device corresponding to an activating one of users,
upon sensing activation of the portable access device, for automatically accessing the network in accordance with activating data, including the remote network address, stored on the portable access device, and thereby for enabling immediate, direct access and transfer of the user-specific data records between the remote processing and storage means and the local processing means,
for automatically generating and, over the network, transmitting to the remote processing and storage means remote, user-specific record requests corresponding to the activating data,
for directly and automatically directing the remote user-specific record requests to the remote network address corresponding to the remote processing and storage means in accordance with the activating data, and
for automatically downloading from the remote processing and storage means via the network the requested user-specific data records of the activating user;
for user-initiated, user-directed and user-controlled reviewing, processing and updating of the downloaded, user-specific data records;

the portable access device forming means both for storing the activating data and for enabling and initiating immediate, direct, automatic accessing of the remote processing and storage means via the local processing means;

and the remote processing and storage means and the portable access device together storing user-specific information sufficient to uniquely identify the user-specific data records associated with the user, the remote processing and storage means thereby being accessible via the network to all users through activation of any local processing means using the respective portable access device.

2. A system as in claim 1 including a plurality of the remote processing and storage means, each located at a respective remote data processing facility, each being connected to the same network, and in which the network is a public network.

3. A system as in claim 1, in which the portable access device includes a user memory and the remote processing and storage means is further provided for changing the contents of the user memory via the network and the local processing means.

4. A system as in claim 1, in which:
the portable access device has a user memory including memory portions containing user identification data and the remote network address; and
the local processing means is further provided for uploading from the portable access device the user identification data and the remote network address.

5. A system as in claim 4, further comprising:
reading means for connecting the portable access device to the local processing means; and in which
the portable access device includes an onboard processor and a user memory that is both readable and writable by the local processing means.

6. A system as in claim 1, in which:
the portable access device has a user memory including a record memory portion containing user record information;
an input device means is connected to the local processing means, for entering into the local processing means data updates; and
the local processing means is further provided for downloading to the portable access device predetermined ones of the data updates for storage in the record memory portion, and for uploading the data updates into the corresponding data records in the remote memory.

7. A system for accessing user data records comprising:
remote processing and storage means that is connected to a publicly accessible network and has a remote network address,
for storing user-specific data records in a remote memory for each of a plurality of users;
for receiving and verifying remote user-specific record requests directed to the remote network address;
for accessing and downloading user-specific data records for each verified remote record request;
for each of a predetermined group of users, a portable access device that has an onboard processor and a user memory including memory portions containing user identification data and a corresponding remote network address;
at least one local processing means:
for sensing activation of the portable access device corresponding to an activating one of users,
upon sensing activation of the portable access device, for automatically accessing the network in accordance with activating data, including the remote network address, stored on the portable access device, and thereby for enabling immediate, direct access and transfer of the user-specific data records between the remote processing and storage means and the local processing means,
for automatically generating the remote record request corresponding to the activating data,
for directly and automatically directing the remote user-specific record request to the remote network address in accordance with the activating data, and
for automatically downloading from the remote processing and storage means via the network memory the user data records of the activating user;
reading means for connecting the portable access device to the local processing means;
the portable access device forming both means for storing the activating data and for enabling and initiating automatic accessing of the remote processing and storage means via the local processing means;
in which:
the remote processing and storage means is further provided for changing the contents of the user memory via the network and the local processing means; and
the local processing means is further provided for uploading from the portable access device the user identification data and the remote network address;
the remote processing and storage means and the portable access device together storing user-specific information sufficient to uniquely identify the user-specific data records associated with the user, the remote processing and storage means thereby being accessible via the network to all users through activation of any local processing means using the respective portable access device.

8. A method for accessing user data records comprising the following steps:
at a remote processor, storing user-specific user data records in a remote memory for each of a plurality of users, each of whom has a member identification code, the remote processor having a remote network address;
for each of a predetermined group of users, storing the corresponding member identification code and predetermined access data in a user memory on a portable access device;
in any of plurality of user non-specific local processing units, sensing activation of the portable access device associated with an activating user;
upon activation of the local processing unit by the portable access device, and, in accordance with the access data stored on the portable input device, directly and automatically accessing a network and automatically generating and applying to the network a remote, user-specific record request corresponding to the activating user's identification code, along with the corresponding remote network address the identification code and remote network address being included in the access data;
at the remote processor, sensing, receiving and verifying the remote record request; and
upon verification of the remote record request, downloading to the local processing unit via the network the user-specific data records that are associated with the activating user from the remote processor to the local processor over the network, review, processing and updating of the downloaded user-specific data records remaining available to and under sole control of the user.

9. A method as in claim 8, in which the step of automatically accessing a network comprises automatically accessing a general, publicly accessible data network.

10. A method as in claim 8, further including the steps of storing portable user data in the user memory of the portable access device and automatically updating the portable user data upon downloading the user data records from the remote processor to the local processor.

11. A method as in claim 8, further including the following steps:
storing user record information in a record memory portion of the portable access device;

entering data updates into the local processor;

downloading to the portable access device predetermined ones of the data updates for storage in the record memory portion; and uploading the data updates into the corresponding data records in the remote memory.

* * * * *